(12) United States Patent
Honeycutt et al.

(10) Patent No.: US 8,579,793 B1
(45) Date of Patent: Nov. 12, 2013

(54) APPARATUS TO AFFECT BRAINWAVE ENTRAINMENT OVER PREMISES POWER-LINE WIRING

(76) Inventors: James David Honeycutt, Vancouver, WA (US); John Clois Honeycutt, Jr., Dallas, TX (US)

( * ) Notice: Subject to any disclaimer, the term of this patent is extended or adjusted under 35 U.S.C. 154(b) by 344 days.

(21) Appl. No.: 13/015,265

(22) Filed: Jan. 27, 2011

Related U.S. Application Data (60) Provisional application No. 61/298,851, filed on Jan. 27, 2010.

(51) Int. Cl.
*A61M 21/00* (2006.01)

(52) U.S. Cl.
USPC .............................................. 600/26; 607/88

(58) Field of Classification Search
USPC .................... 600/26–28, 300; 607/45, 66, 88; 340/575; 455/402
See application file for complete search history.

(56) References Cited

U.S. PATENT DOCUMENTS

| | | | |
|---|---|---|---|
| 4,471,399 A | 9/1984 | Udren | |
| 4,479,215 A | 10/1984 | Baker | |
| 4,802,057 A | 1/1989 | Patterson | |
| 5,251,191 A | 10/1993 | Sturzl | |
| 5,491,463 A | 2/1996 | Sargeant | |
| 7,199,706 B2 | 4/2007 | Dawson | |
| 7,463,877 B2 | 12/2008 | Iwamura | |
| 7,627,304 B2 | 12/2009 | Koga | |
| 2006/0206174 A1* | 9/2006 | Honeycutt et al. | 607/88 |

OTHER PUBLICATIONS

U.S. Appl. No. 11/307,348, filed Sep. 14, 2006, Honeycutt.
U.S. Appl. No. 11/949,717, Honeycutt.

* cited by examiner

*Primary Examiner* — Charles A Marmor, II
*Assistant Examiner* — Laura Fajardo (57) ABSTRACT

This invention discloses an apparatus and method to affect brainwave entrainment by Very Low Frequency eXclusive-OR (XOR) modulation of a Very High Frequency carrier over a premise's power-line Alternating Current (AC) wiring. A microcontroller with stored program memory space is used to store and produce the waveforms that lead to brainwave entrainment by controlling an H-Bridge capable of generating bipolar square waves, which output is capacitive coupled to a premises AC power-line and a light sensing device is used by the microcontroller to determine whether to produce daytime or nighttime entrainment frequencies.

14 Claims, 11 Drawing Sheets

Figure 2a. Prior Art – Mono-Polar AND Modulated PWM PLC Driver

Figure 2b. Prior Art Waveforms – Mono-Polar AND Modulated PWM Pulses

Figure 3a. Prior Art – Mono-Polar AND Modulated PWM PLC Driver

Figure 3b. Prior Art Waveforms – Mono-Polar AND Modulated PWM Pulses

Figure 4a. New Apparatus - Bipolar XOR Modulated PWM Using H-Bridge

Figure 4b. New Apparatus Waveforms - Bipolar XOR Modulated PWM Using H-Bridge

Figure 5. Preferred Embodiment

Figure 6. Typical 60 Hz 120 VAC Power Line Waveform

Figure 7. 60 Hz 120 VAC Power Line Detail of 2 Microseconds

Figure 8. 60 Hz 120 VAC Power Line with XOR Modulated 2MHz Carrier

Figure 10. 60 Hz 120 VAC 2μS Detail of 2 MHz Carrier at 5 Volts

Figure 11. Software Flowchart

APPARATUS TO AFFECT BRAINWAVE ENTRAINMENT OVER PREMISES POWER-LINE WIRING

CROSS-REFERENCE TO RELATED APPLICATION

This application claims the benefit of U.S. Provisional Application No. 61/298,851, filed Jan. 27, 2010. The foregoing application is herein incorporated by reference in its entirety.

FIELD OF THE INVENTION

This invention relates to the field of using a microcontroller with stored program memory space to produce waveforms to control an H-Bridge, which is capacitive coupled to a premise's AC power-line wiring to emit a non-sensory electromagnetic signal to affect brainwave entrainment by Very Low Frequency eXclusive-OR (XOR) modulation of a Very High Frequency carrier signal.

BACKGROUND OF THE INVENTION

Brainwave entrainment occurs when observable and measureable brainwave activity follows the repetitious patterns of external stimulus. Sensory forms of entrainment, including visual stimulation as from a flickering candle or auditory stimulation as from a dripping faucet, can lead a person into a trancelike state. This state can often occur during highway driving, causing the common phenomena of "highway hypnoses." Such trancelike states can be confirmed with electroencephalography (EEG) which monitors a subject's brainwave activity, where the brainwave activity mimics that of sleeping brainwaves.

Figure 1:
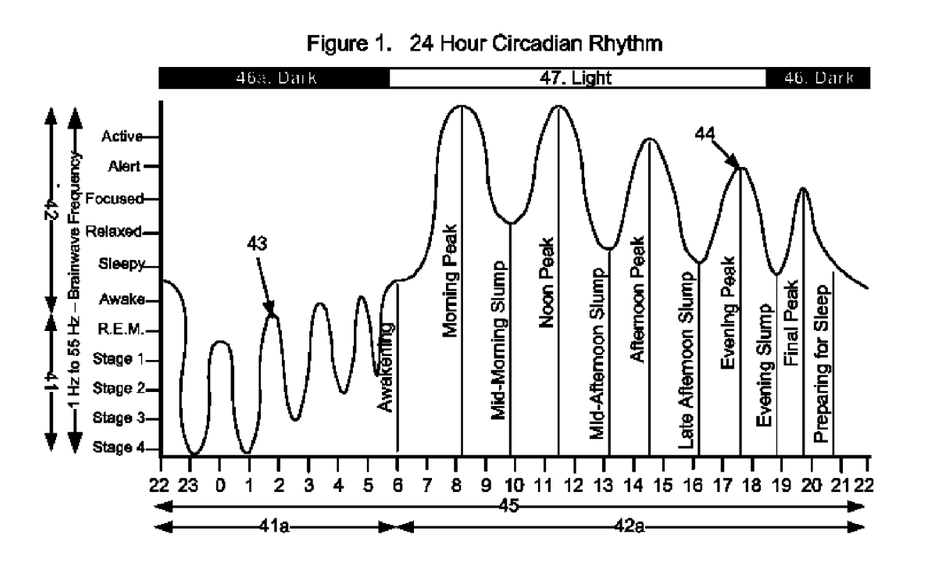
FIG. 1 shows a complete 24 hour Circadian Rhythm for humans.

It has been shown that human brainwaves have standardized patterns which are consistent from day to day. These patterns, or rhythms, are referred to as circadian rhythms when the patterns have a period of twenty-four hours before repeating. Periods or cycles with approximately ninety-minutes are referred to as ultradian rhythms. While the specific brain activity of any given ultradian rhythm can vary, the general patterns are consistent within the larger circadian rhythm. These ultradian rhythms have been widely studied for night cycles and have common names such as 'Stage 1', 'Stage 2', and 'REM' sleep. Similarly, there exist ultradian cycles for daytime cycles. Daytime ultradian rhythms are typically identified by measuring the core body temperature of a mammal, as ambulatory EEG monitoring is both expensive and invasive. Such daytime ultradian rhythms may be recognized intuitively as most people experience the typical mid-morning and mid-afternoon slumps in energy, as well as accompanying peaks in activity. FIG. 1 shows a complete circadian rhythm with both day and night ultradian cycles.

Over time, however, the ultradian rhythms observed during sleep cycles tend to flatten out, resulting in poorer sleep. Furthermore, one can lose the natural rhythms of sleeping, waking, and living which produce a healthy and happy lifestyle. What is desired then is a way to emulate healthy brainwave activity in such a way as to cause entrainment, such that brainwave activity remains or returns to healthy levels.

There exists technology to perform brainwave entrainment; however these iterations fail in significant ways. For example, most iterations fail to provide a bi-polar based signal, fail to base these brainwave entrainments on natural therapeutic healing frequencies following natural circadian and ultradian rhythms, and fail to modulate the signals with a Pulse Width Modulation (PWM) using an eXclusive OR (XOR). Those iterations which do use bi-polar, XOR modulated natural healing frequencies, particularly those disclosed in U.S. patent application Ser. Nos. 11/307,348 and 11/949,717, lack the ability for one to receive the frequency stimulations necessary for brainwave entrainment unless one is within a very short distance of, or even touching, the entrainment apparatus. It is desirable then, to have a bi-polar, natural therapeutic frequency based circadian rhythm, XOR modulated brainwave entrainment device where one can receive the entrainment signals without being tethered to an apparatus, but rather can receive these signals while present at a given premises.

BRIEF SUMMARY OF THE INVENTION

The invention disclosed and claimed herein addresses the above and other needs and provides means to achieve brainwave entrainment in mammals, including humans, within a premises using the AC power-line wiring. Rather than simply creating a trancelike state in the humans and animals within the premises, the present invention establishes a twenty-four hour circadian rhythm supportive of a mammal's internal circadian and subsequent ultradian rhythms for improved sleep and improved awake periods. A light sensitive photosensor is used to determine ambient light levels within the premises, which information is then transmitted to a microcontroller. The microcontroller, clocked by a quartz crystal with a fundamental resonance frequency very close to a Fibonacci number, then generates frequencies selected to induce brainwave entrainment either in support of natural sleep cycles during periods of relative darkness or in support of learning, expanded awareness and relaxation during periods of relative lightness. These frequencies, one significantly higher than the other, are then XOR modulated using an H-bridge. The output of the H-Bridge is then capacitive coupled to a premise's AC power-line.

The verified field of coverage includes a dwelling with 110 to 240 volts AC two-phase wiring in living and working spaces, with no single wiring run exceeding 100 meters from the apparatus' connection to the power-line, and the overall load not exceeding 250 Amps for a single apparatus. Multiple apparatuses may be used for dwellings exceeding these limitations.

DETAILED DESCRIPTION

The invention of this instance is designed to induce brainwave entrainment following the twenty-four hour daily Circadian Rhythm as depicted in FIG. 1. The Light 47 and Dark 46 and 46a legend at the top of the figure indicate the relative light and dark periods of the daily cycle, where non-nocturnal mammals are awake during the light 47 periods and asleep during the dark 46 and 46a periods. Sleep Stages 41 and Awake Ranges of brainwave activity 42 are shown on the left side of the figure. These stages 41 and ranges 42 relate to relative brainwave frequencies in the range of 1 Hz to 55 Hz as observed in EEG monitoring. An hourly scale 45 is depicted across the bottom of the figure starting at 22:00 hours (10 PM on the left and running for twenty-four hours ending at 22:00 hours the next day on the right. Period 41a shows the classical circadian rhythms of sleeping, which are correctly termed ultradian rhythms of sleep. Period 42a shows the inventors observed daytime ultradian rhythms with their respective period names. 43 represents the brainwave ranges during sleep and 44 represents the brainwave activity when awake for non-nocturnal mammals.

The present invention induces brainwave entrainment by modulating a Very High Frequency (VHF) carrier signal that is injected over a premise's AC power-line wiring and XOR modulating it with a Very Low Frequency (VLF) square wave following the observed and plotted brainwave frequencies of 1 to 55 Hz depicted in FIG. 1. Additionally, the present invention may also use higher frequency harmonics in the range of 55 Hz to 5,000 Hz of the lower frequency brainwaves in order to extend the effective range of the emitted signals over the power-line.

Figure 2A:
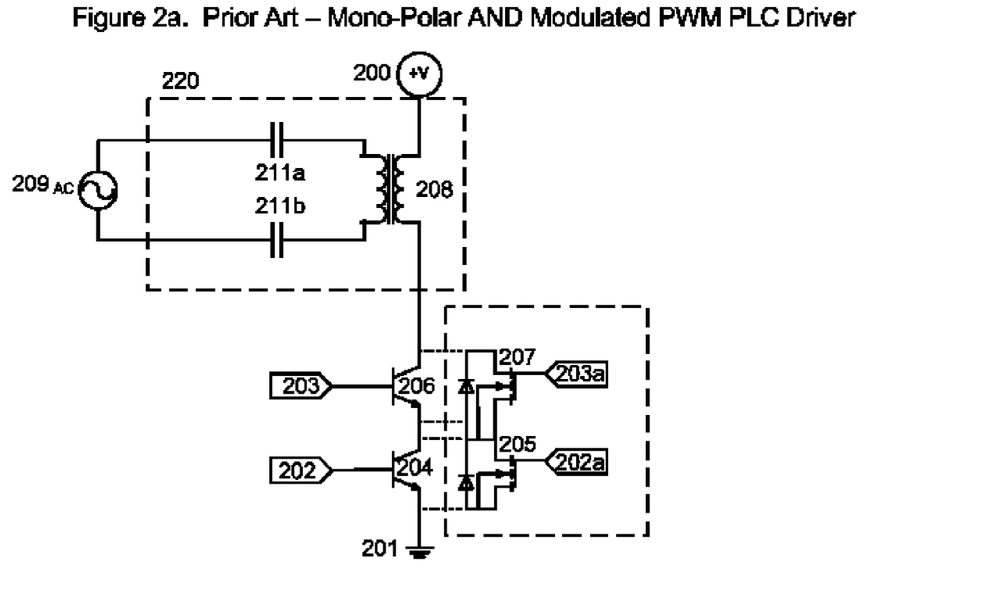
FIGS. 2a and 2b show the typical prior art and result waveforms.
Figure 2B:
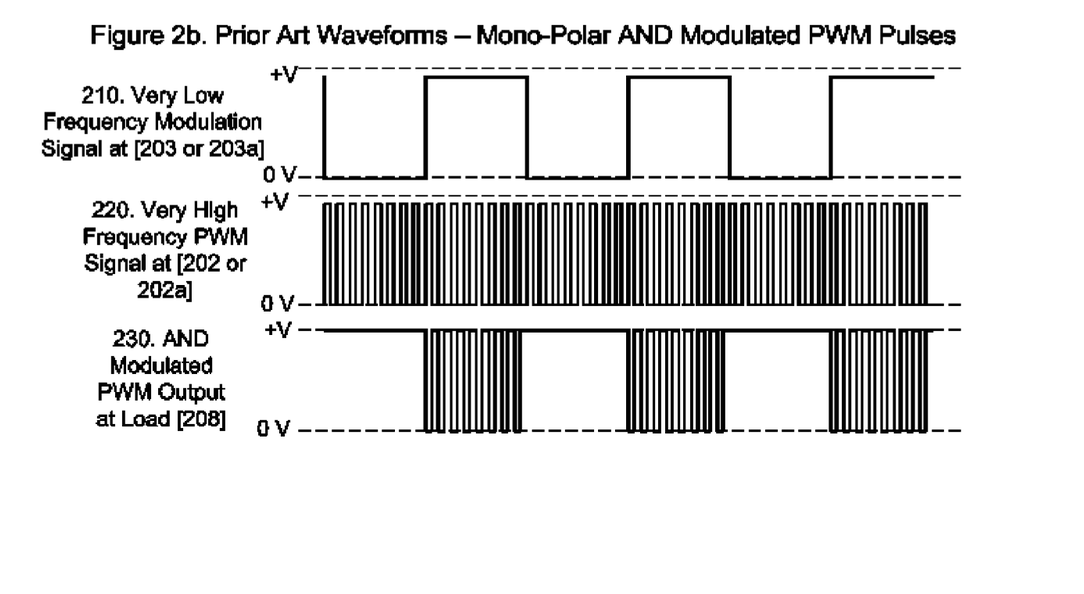
Figure 3A:
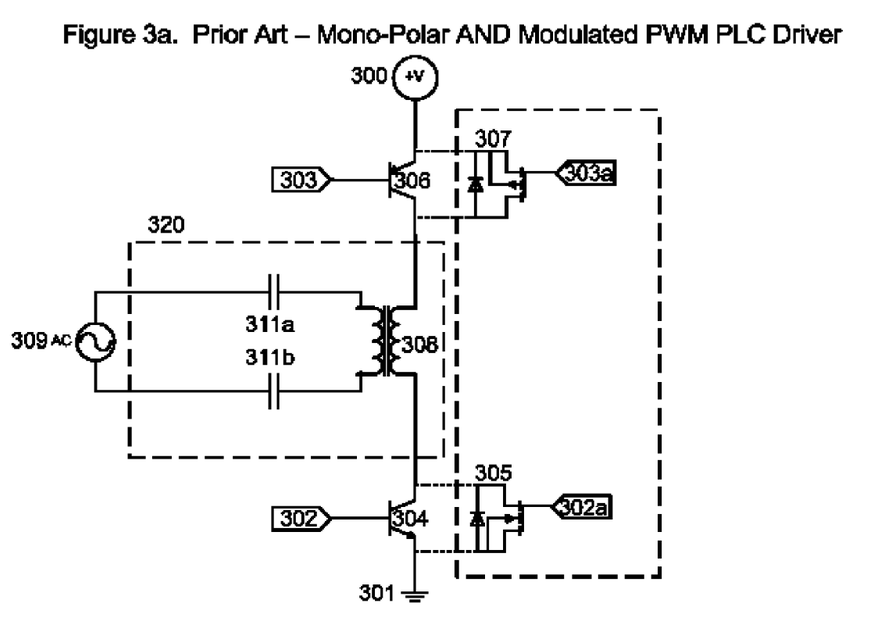
FIGS. 3a and 3b show the prior art with a PWM signal added.
Figure 3B:
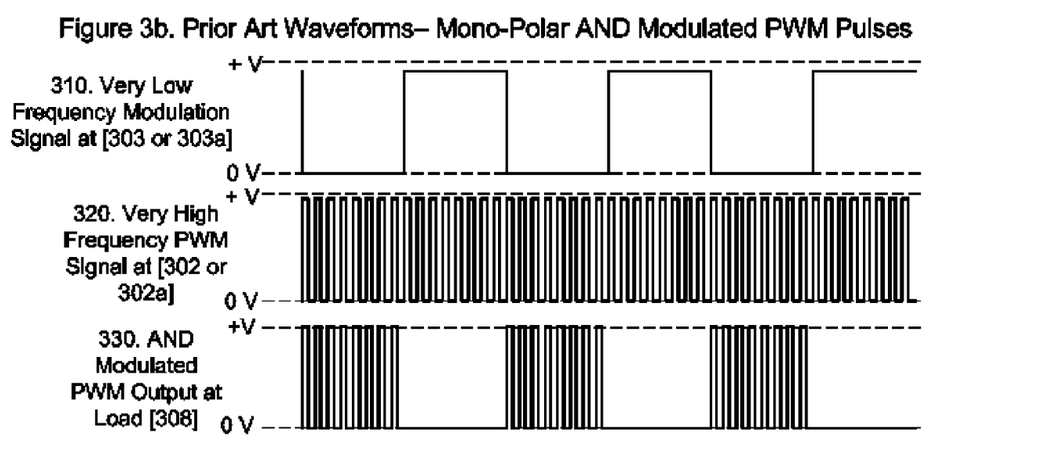

Existing apparatuses and methods rely upon methods different than the present invention's to modulate a carrier wave over a premise's power-lines. In all cases where a carrier signal is modulated in the related art the modulated signal is logically AND'd with the higher frequency carrier signal. FIGS. 2a and 3a represents the prevalent prior art of all such devices using what is commonly called in this field as a Power-Line Communication (PLC) interface. As shown in FIG. 2a typical PLC 220 consists of a line matching transformer 208 and non-polarized high voltage capacitors 211a and 211b to connect one side of the transformer 208 to the premise's AC power-line 209. The lower frequency modulating input 203 or 203a is logically AND'd with the VHF carrier signal input (202 or 202a) to cause current to flow from +V 200 through transistors 204 and 206 or MOSFETs 205 and 207. FIG. 2b shows the resultant waveforms created across load 208 of the line matching transformer, illustrating the logical AND function. FIG. 3a illustrates the same type of PLC 320 being driven by a different transistor 304 and 306 or MOSFET 305 and 307 arrangement, and still using a logical AND function as shown in the resulting waveforms in FIG. 3b.

Figure 4A:
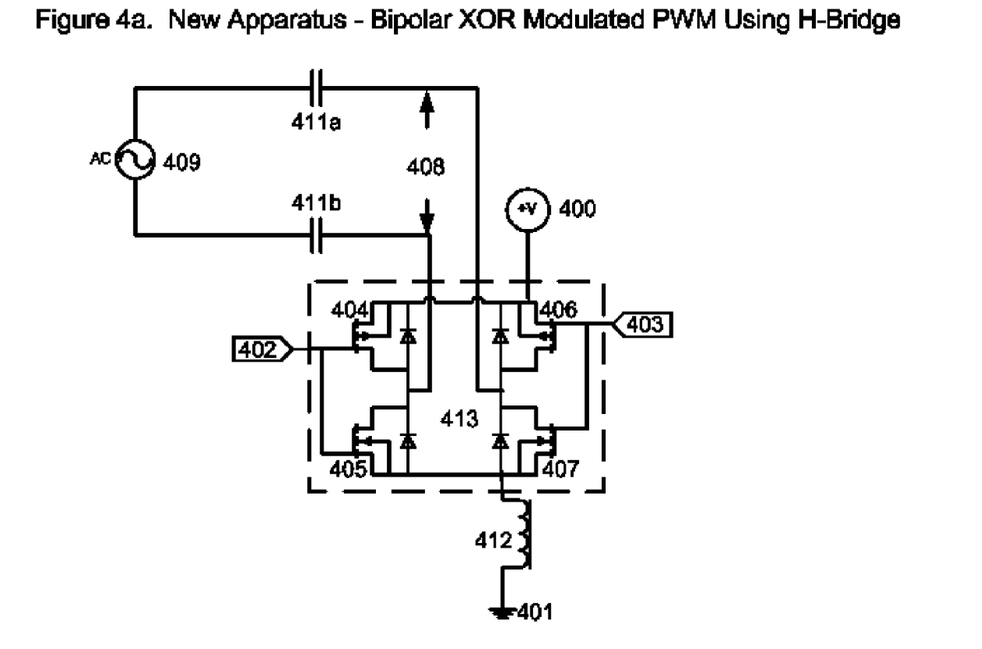
FIG. 4 shows the new art for the invention of this instance.
Figure 4B:
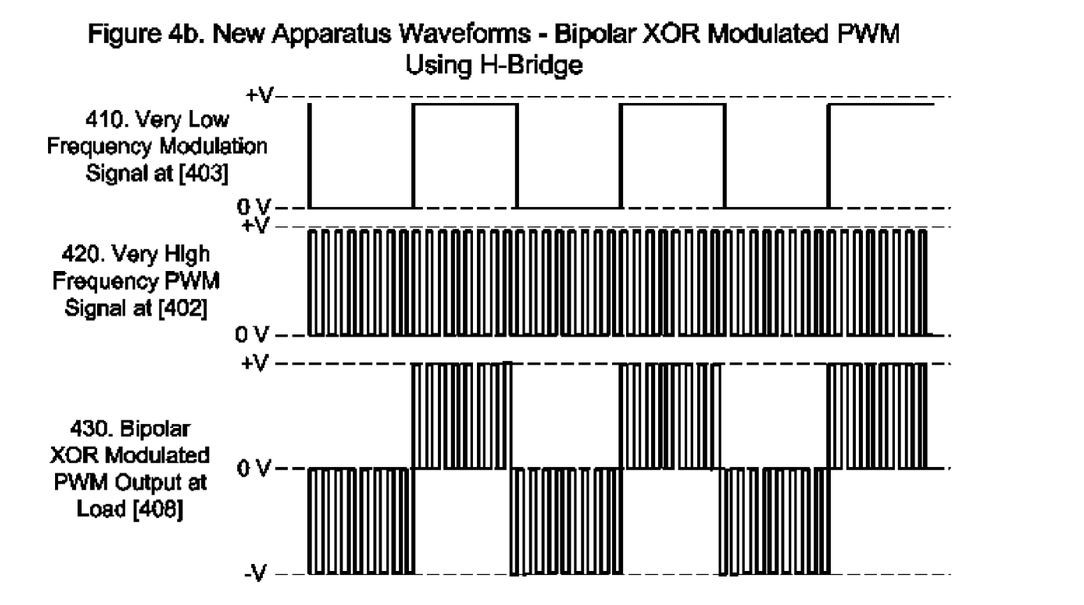
Figure 5:
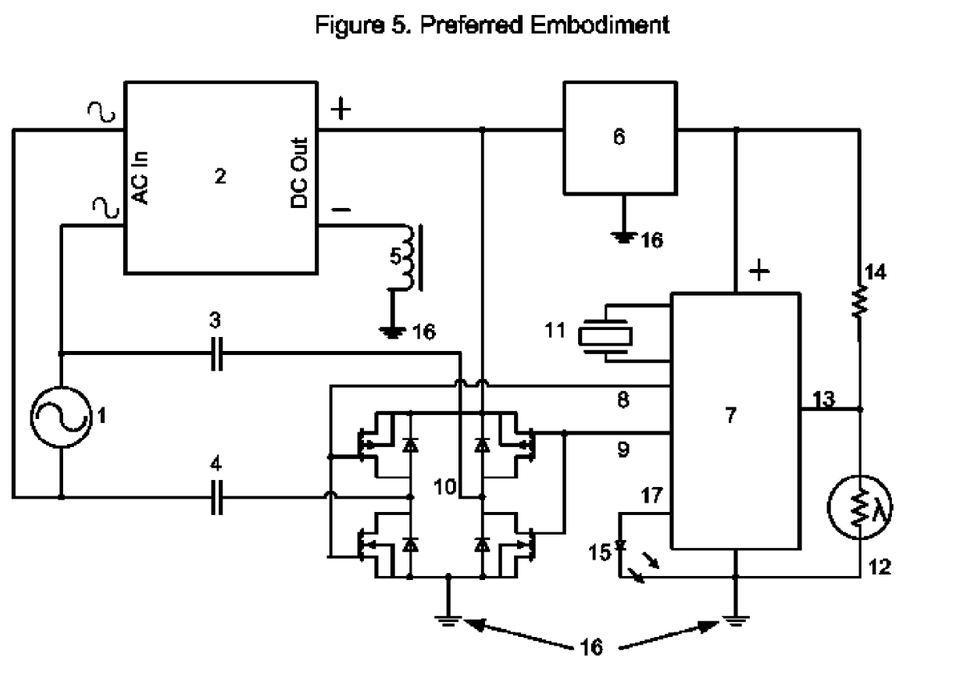
FIG. 5 shows the preferred embodiment of the invention of this instance.

Premises power-line specific carrier wave frequencies XOR modulated with lower frequencies make it possible to induce brainwave entrainment in all mammals within the premises using the present invention as shown in FIGS. 4a, 4b and 5. The use of the high current capable MOSFET H-Bridge 413 (comprised of MOSFETs 404, 405, 406 and 407 shown within the dashed line) and correctly selected capacitances for line coupling capacitors 411a and 411b based upon the carrier frequency allow the line matching transformer (not required in this invention) which is commonly used in PLCs to be removed. Inductor 412 is added to the ground connection of the H-Bridge to reduce transients occurring on the AC power-line 409. All four of the MOSFETs are protected with reverse bias diodes across their respective source and drain connections as shown in FIG. 4. The H-Bridge 413 is connected to the +V DC power source 400 and through inductor 412 to ground potential 401. Input 402 is connects to the VHF PWM carrier signal 420 and input 403 connects to the VLF modulating signal 410. 408 represents the effective load across the bipolar output of H-Bridge 413. FIG. 4b shows the resultant unique wave forms produced using this XOR modulation and H-Bridge line driving technique. 410 is the square wave modulating signal that feeds input 403 of H-Bridge 413. 410 is generally a 50% duty cycle square wave at the desired frequency intended to cause brainwave entrainment and is generally between 1 Hz and 5,000 Hz. While monitored brainwave frequencies tend not to exceed 50 Hz, this apparatus supports higher resonant multiples of the brainwave frequencies between 1 and 50 Hz to support a greater range of distance between the subject mammals and the emitting premises power-line wiring. 420 is the variable duty cycle PWM square wave carrier signal and is selected to be high enough in frequency, generally between 500 KHz and 2.4 MHz, to overcome the effective of inductive loading on the premise's power-lines, and to support the capacitive coupling to the power-line. 430 is the resulting bipolar XOR modulated square wave observed across load 408.

The apparatus of the present invention is depicted schematically in FIG. 5. AC Line 1 represents the connection between the apparatus and the premises power-line. This connection 1 provides both the source power for the apparatus' AC to DC power supply 2 and the connection point to apparatus' line coupling capacitors 3 and 4. Power Supply 2 provides a stepped-down and regulated direct current power source for the MOSFET H-Bridge 10 and for Voltage Regulator 6 which is used to further reduce the direct current voltage to meet the operating requirements of Microcontroller 7. Inductor 5 connected between the negative output of Power Supply 2 and the apparatus' ground reduces the transients that may appear across AC Line 1 and reduces the affect of these transients on the entire apparatus. Line coupling capacitors 3 and 4 are non-polarized capacitors with a working voltage of at least two times the AC line 1 voltage. Photocell 12 provides ambient lighting information by changing the voltage that appears on Analog to Digital Conversion (ADC) Input 13 through Bias Resistor 14. LED indicator 15 provides a simple operation indication. Fibonacci Number Quartz Crystal 11 provides the precision timing for operating Microcontroller 7. Microcontroller 7 has stored program capabilities along with the ability to produce a VHF PWM square wave signal 8 that is XOR'd with a lower frequency modulation square wave signal 9.

Microcontroller 7 must be capable of generating a precision Very High Frequency carrier square wave generated as a duty cycle variable Pulse Width Modulation signal 8 in the range of 500 Kilohertz to at least 2.4 Megahertz, which is output to one input of the MOSFET H-Bridge 10 shared gates. The duty cycle must be variable to support variations in the VHF carrier and line coupling capacitors to reduce the load across the H-Bridge output. Higher duty cycles also may be needed to extend the range of the emitted entrainment signals. Microcontroller 7 must also be capable of generating a precise very low frequency modulation signal 9 as a constant 50% duty cycle square wave in the range of 1 Hertz to 5,000 Hertz, which is output to the other shared gated input of the MOSFET H-Bridge 10.

The two outputs of the MOSFET H-Bridge line driver 10 are capacitive coupled to the AC Power-Line source 1 using a preferred value of 10,000 picofarads 1,000 Volt capacitors 3 and 4. The values of the line coupling capacitors 3 and 4 are selected to provide a large resistance to the 50 to 60 Hertz AC component frequency, while simultaneously presenting a low resistance to the 500 Kilohertz to 2.4 Megahertz carrier frequency. Values for capacitors 3 and 4 may fall between 1,000 picofarads to 470,000 picofarads and should be rated for a working voltage of at least two times the AC line 1 voltage. The formula for determining the relative resistive impedance, or reactance of capacitors 3 and 4 is 1/(2piFC) where F is Frequency in Hertz and C is Capacitance in Farads. Thus, for a capacitance of 10,000 picofarads the reactive impedance at 2,000,000 Hz is 7.958 ohms and at 60 Hz it is 265,258 ohms.

The preferred frequency of Fibonacci Crystal 11 used to provide the timing element for Microcontroller 7 is 24 Megahertz as it within one percent (1%) of a Fibonacci Number and sufficiently high enough to provide the effective clocking frequency for Microcontroller 7 to enable it to generate the required VHF carrier PWM signal. The inventors have found that all apparatuses used to generate electrical signals designed to interact with living, organic systems should use only quartz crystals whose fundamental frequency is as close as practically possible with modern manufacturing techniques to a natural Fibonacci number, typically within one percent. 24 Megahertz is such a frequency, being less than one percent from 24,157,817 which is a Fibonacci number.

Power Supply 2 provides power to the apparatus by converting the incoming 240 VAC to 110 VAC 50 Hz to 60 Hz line power to a regulated DC voltage in the range of five to twenty-four volts and is capable of maintaining regulation within ten percent of the desired DC voltage at a minimum of 0.5 Amps of DC current.

Photocell 12 is connected to Microcontroller 7 using an analog to digital converting (ADC) capable input 13 and is used to determine ambient light levels within the premises, such ambient light levels being used to affect the stored program causing it to generate either daytime or nighttime ultradian signals when the premises are respectively light or dark. Bias Resistor 14 provides a positive voltage reference for ADC input 13.

In the preferred embodiment a 12 VDC switching type power supply 2 is used to step-down the 240 VAC to 110 VAC 50 Hz to 60 Hz alternating current source to 12 volts direct current for the apparatus' power supply. The 12 VDC is used to power the high current capable MOSFET H-Bridge line driver 10 and is further reduced by a low dropout (LDO) power regulator 6 which provides a regulated 3.3 VDC to Microcontroller 7. Light Emitting Diode (LED) 15 is connected to an output port 17 on Microcontroller 7 capable of directly driving LED 15. A series resistor (not shown) may be used to reduce the current to LED 15 to prevent it from being damaged and to protect output port 17 from too much current being drained or sourced.

Figure 6:
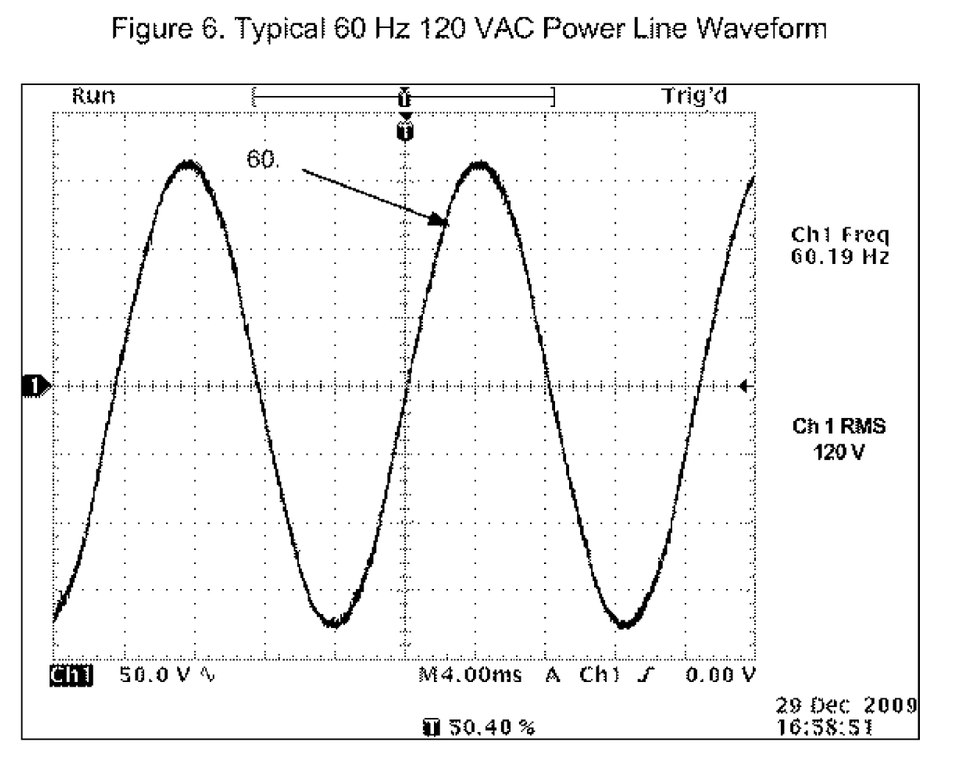
FIG. 6 shows an oscilloscope capture of an idle power-line.
Figure 7:
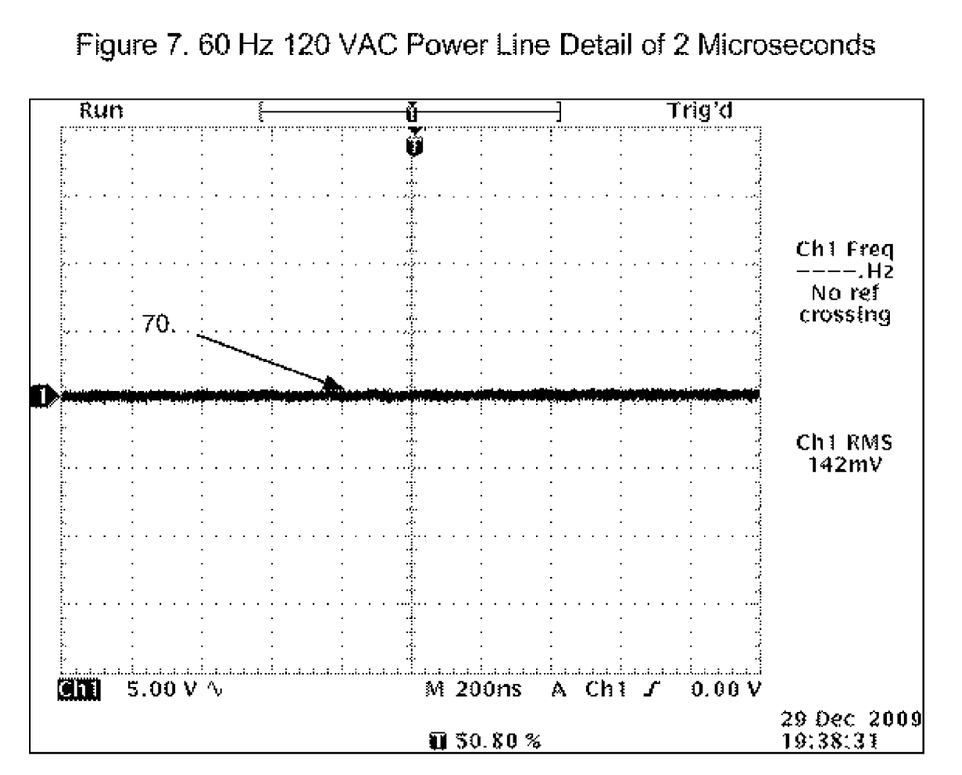
FIG. 7 shows an oscilloscope capture of the detail of an idle power-line.

Injecting low frequencies over premises AC power-lines is problematic due to both the 60 Hertz (Hz, or cycles per second frequency) nature of alternating current (or 50 Hz in other areas of the world) and varying inductive and resistive loads present on the power-lines. Most AC line modulation schemes have been adopted for either carrying audio (as in power-line intercom or telephone extensions) or data (as in HPNA or X10) from a transmitting source to a receiving station, or even a transceiver application. While the apparatus and methods presented in this invention may be applied to these applications, the primary application of the present invention is to cause brainwave entrainment in mammals within homes and other buildings. It is critical whenever imposing a carrier wave on a premise's AC power-line wiring that such injected signals do not interfere with the operation of equipment or appliances connected to the same AC power-line. FIG. 6 is an oscilloscope capture of a typical US 120 VAC 60 Hz power-line sine wave 60 without the apparatus of the present invention attached to the line. FIG. 7 is a detailed 2 microsecond portion 70 of the same power-line as shown in FIG. 6, again without the present invention attached to the line. These two FIGS. 6 and 7, establish the baseline images of a typical premise's AC power-line waveforms.

Figure 8:
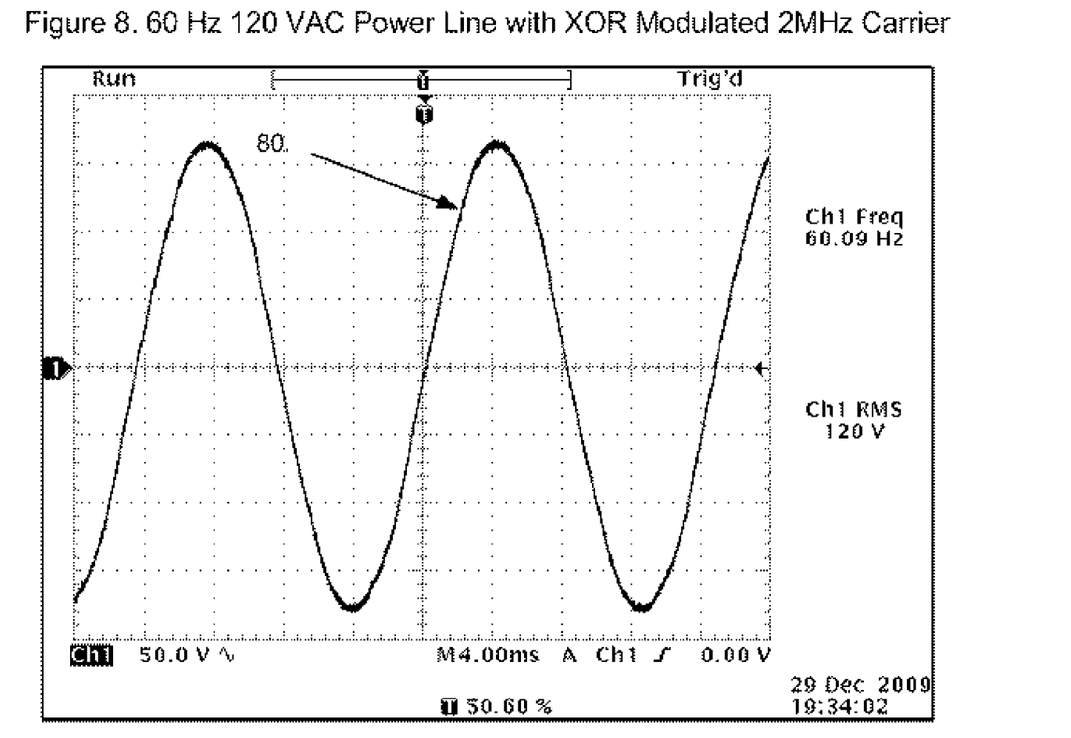
FIG. 8 shows an oscilloscope capture of an XOR modulated power-line.

FIG. 8 shows the same premise's AC power-line waveform 80 with the apparatus of the present invention attached to the power-line and actively producing a 2,000,000 Hz carrier signal that is XOR modulated with a 440 Hz square wave. There is no noticeable disruption of the baseline AC power-line waveform 60 as seen in 80. Subsequent monitoring and testing of typical appliances and AC powered devices in the premises, including digital televisions, analog televisions, desktop and laptop personal computers, ranges, refrigerators, air conditioners and the like showed no observable or measurable affects to these by the present invention being actively connected to the power-line.

Figure 9:
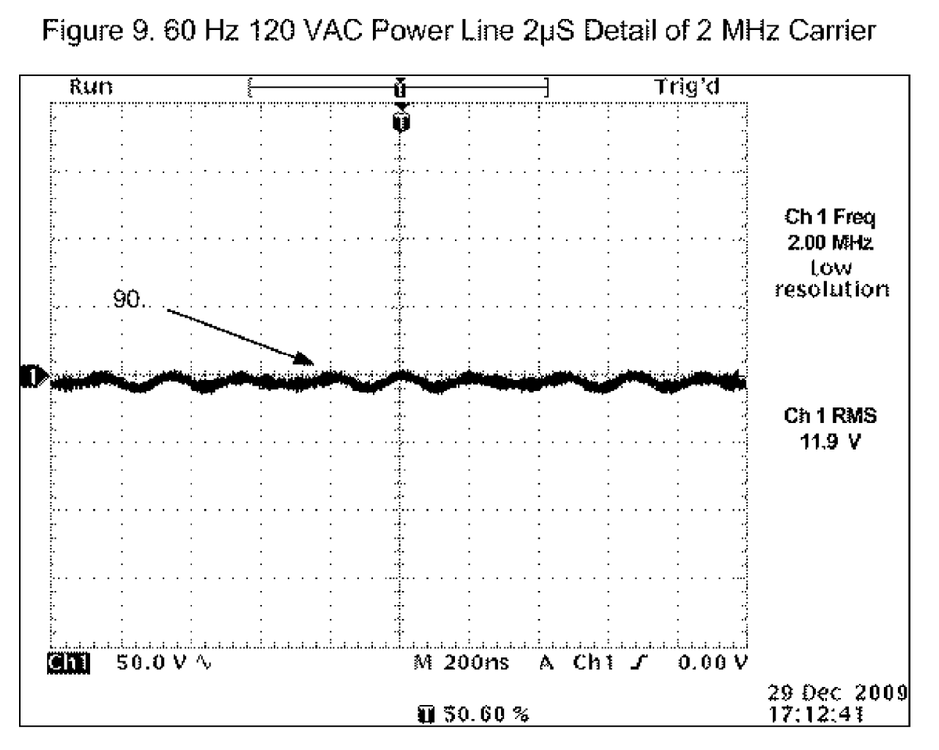
FIG. 9 shows an oscilloscope capture of the detail of an XOR modulated power-line.
Figure 10:
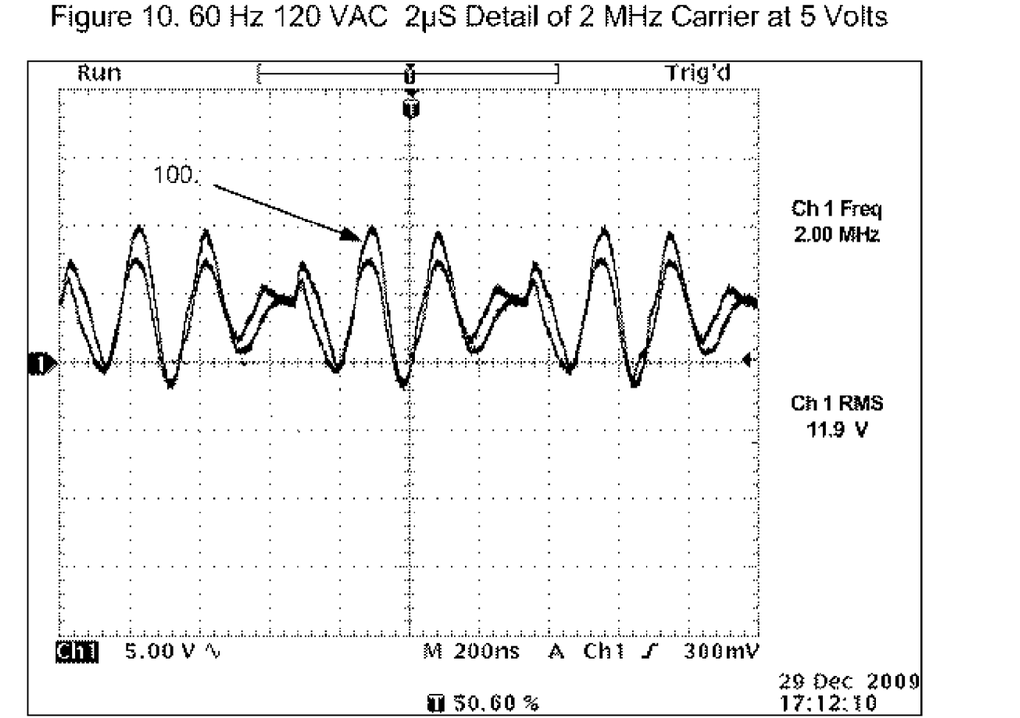
FIG. 10 shows an oscilloscope capture of more detail of an XOR modulated power-line.

FIG. 9 details a 2 microsecond portion 90 of the same power-line waveform with the apparatus of the present invention actively connected to the power-line. Modulation of the power-line can be seen within this segment 90 in the range of about twelve volts. FIG. 10 is the same 2 microsecond detailed segment 90 of the power-line waveform with the voltage per division of the oscilloscope reduced from 50 volts to 5 volts. Definite modulation of the AC power-line 100 can be seen in the range of twelve volts. This range of modulation will vary based upon loading of the AC power-line.

As further evidence of the modulation, the carrier frequency was reduced from 2,000,000 Hz to 1,500,000 Hz which is in the receiving range of Amplitude Modulated (AM) radio receivers. The apparatus of the present invention was connected to the power-line wiring and activated with a 440 Hz XOR modulated square wave and an AM radio was tuned to 1,500,000 Hz and the AM radio audibly demodulated the 440 Hz square wave as heard over its speaker. The AM radio was then used to validate the existence of the modulated carrier waver throughout the premises. Similar AM radio receivers were subsequently used to validate the effective range of the apparatus both inside and outside the premises, and it was discovered the effective radio frequency range of the apparatus was limited to the premises itself and a 2 meter perimeter outside the physical premises. No indication was found of any back-feeding of the signal into neighboring premises.

As evidence of the achievement of brainwave entrainment, the apparatus of the present invention was installed in a home on its AC power-line wiring in an area away from the sleeping quarters. Persons in the home used an ambulatory EEG sleep monitoring system to record their sleep patterns and these were compared to the timing and signals produced by the present invention and it was found that the recorded brainwave signals followed the apparatus' generated XOR modulated nighttime signals. Subsequent sleep monitoring without the present invention active showed irregular sleep patterns, confirming the present invention did induce brainwave entrainment.

Figure 11:
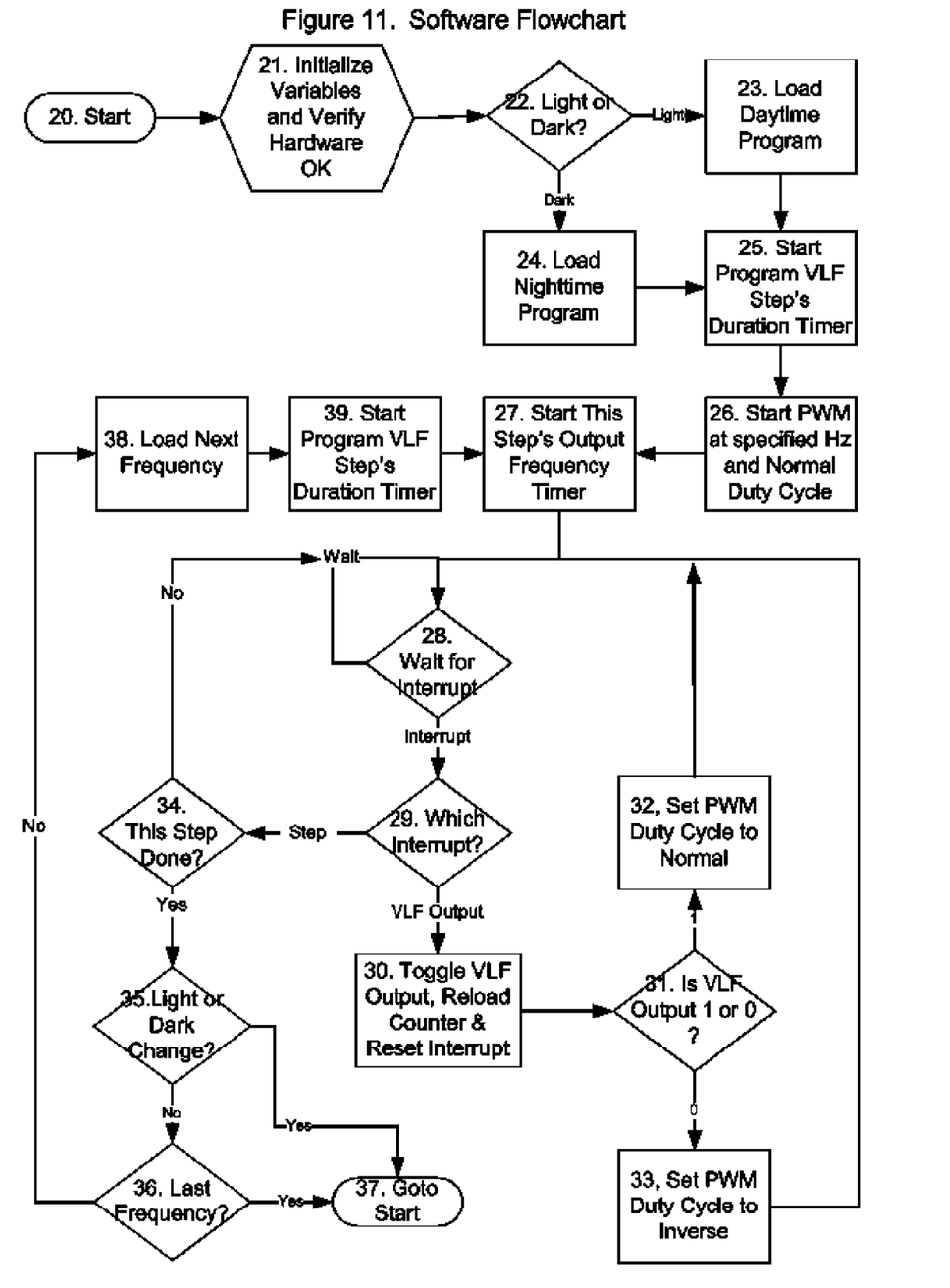
FIG. 11 shows software flowchart for the microcontroller's stored program.

FIG. 11 is the software flowchart for the stored program in Microcontroller 7. The software starts at step 20 and upon initialization 21 the firmware verifies the hardware is operational by validating internal and external signals and then measures the ambient light levels at 22 on ADC input 13. If ADC input 13 is within the daytime light levels control passes to step 23 and the daytime program steps are loaded. If the ADC input 13 is within nighttime light levels control passes to step 24 and the nighttime program steps are loaded. Both steps 23 and 24 pass control to step 25 where a programmatic step duration timer is started. Control passes to step 26 and the PWM Carrier signal is turned on at the normal duty cycle. Duty cycles of the PWM will change based upon the state of the lower frequency modulation signal to maintain a consistent 'On' time for the H-Bridge if a duty cycle other than 50% is used. Selection of the duty cycle is tied to the selection of the line coupling capacitor values and driving capabilities of the specific H-Bridge. A longer duty cycle requires a higher driving capability and a lower capacitance to avoid damaging the H-Bridge or creating unwanted signals on the AC power-line.

At step 27 a second timer is started based upon the frequency of modulated lower frequency and the modulated lower frequency is set to a logical one (1). Control is passed to step 28 and the processor waits for an interrupt. At step 29 the processor determines which interrupts occurred. If the step timer completed, which is typically in the range of 1 to 5 minutes control is passed to step 34. If the VLF modulation frequency timer expired control is passed to step 30. At step 30 the VLF modulated frequency timer the interrupt is reset and the VLF output is toggled from either a 1 to 0 or a zero to a 1, depending upon its current state. Step 31 determines the new state of the VLF output and If the VLF output is now a 0 control is passed to step 33 and the duty cycle of the PWM output is inverted. If the VLF output is now a 1 control is passed to step 32 and the PWM duty cycle is retuned to its normal value. Both steps 32 and 33 resume operation waiting for an interrupt at step 28.

If step 29 determined the interrupt is the step timer, the software passes control to step 34 and the processor determines if this step is completed. If not then the step timer is reset and control is passed to step 28 to wait for another interrupt. If the step is done control passes to step 35 and the ADC input level is checked to see if there was a change in ambient light levels from the previous check. If there was a change the software restarts by going to Start at step 20 to confirm the light change and load the appropriate daytime or nighttime program. If there was no change the control is passed to step 36 and the software checks if this is the last frequency, or step, for this program. If it is the last step then the software returns to the start 20. If it is not the last step then control is passed to step 38 to load the next step then step 39 sets its timer and the program resumes waiting on an interrupt at step 28.

| Definition List 1 | |
|---|---|
| Term | Definition |
| AC | Alternating Current |
| ADC | Analog to Digital Converter |
| AM | Amplitude Modulated |
| DC | Direct Current |
| EEG | Electroencephalography |
| HPNA | Home Power-line Network Access |
| Hz | Hertz—Cycles Per Second |
| LED | Light Emitting Diode |
| MOSFET | Metal Oxide Substrate Field Effect Transistor |
| PLC | Power-line Communication |
| PWM | Pulse Width Modulation |
| VHF | Very High Frequency (above 100,000 Hz) |
| VLF | Very Low Frequency (below 10,000 Hz) |
| XOR | eXclusive OR logical function |

What is claimed is:

1. An apparatus for entraining brainwaves in mammals, comprising:
    a microcontroller;
    a quartz crystal for clocking the microcontroller;
    a storage device storing one or more programs, said programs being timed frequency sequences corresponding at least in part to an ultradian brainwave activity pattern of mammals; and
    the storage device further storing instructions for controlling the microcontroller to perform steps comprising:
        producing a first square wave signal having a first frequency based at least in part upon the quartz crystal and an ultradian brainwave activity pattern of mammals in said one or more stored programs;
        producing a second square wave signal having a second frequency based at least in part upon said one or more stored programs and the quartz crystal wherein the second square wave signal's frequency is greater than the first square wave signal's frequency;
    producing a mixed bi-polar square wave signal by mixing the first square wave signal and the second square wave signal through an H-bridge acting as an eXclusive OR (XOR) to modulate the first and second square wave signals;
    injecting the mixed bi-polar square wave signal on to a premises' power-line.

2. The apparatus of claim 1, wherein the quartz crystal has a fundamental resonance frequency which is less than 1% from a Fibonacci number in the range of 75,000 Hz to 102,000,000 Hz.

3. The apparatus of claim 1, wherein said one or more stored programs contain tables for generation of both daytime and nighttime ultradian brainwave activity patterns for mammals.

4. The apparatus of claim 1, wherein the microcontroller utilizes a photo-sensor to measure ambient light levels in the premises to select a program from the one or more stored programs to produce either daytime or nighttime ultradian brainwave activity pattern signals.

5. The apparatus of claim 1, wherein a premises power-line is capacitively coupled to the mixed bipolar square wave signal using non-polarized capacitors rated at least two times the RMS voltage of the premises power-line and between 1,000 and 470,000 picofarads.

6. The apparatus of claim 1, where the second frequency is in the range of 500,000 Hz to 2,400,000 Hz.

7. The apparatus of claim 1, where the first frequency is in the range of 1 Hz to 500,000 Hz.

8. An apparatus for entraining brainwaves in mammals, comprising:
    a microcontroller;
    a means for clocking the microcontroller at a frequency within 1% of a Fibonacci number in the range of 75,000 Hz to 102,000,000 Hz;

a storage device storing one or more programs, said programs being timed frequency sequences corresponding at least in part to an ultradian brainwave activity pattern of mammals; and the storage device further storing instructions for controlling the microcontroller to perform steps comprising:

producing a first square wave signal having a first frequency based at least in part upon the microcontroller's clocking frequency and ultradian brainwave activity patterns of mammals in said one or more stored programs;

producing a second square wave signal having a second frequency based at least in part upon the one or more stored program and the microcontroller's clocking frequency wherein the second square wave signal's frequency is greater than the first square wave signal's frequency;

producing a mixed bi-polar square wave signal by mixing the first square wave signal and the second square wave signal through an H-bridge acting as an eXclusive OR (XOR) to modulate the first and second square wave signals;

injecting the mixed bi-polar square wave signal on to a premises power-line.

9. The apparatus of claim 8, wherein said one or more stored programs contain tables for generation of both daytime and nighttime ultradian brainwave activity patterns for mammals.

10. The apparatus of claim 8, wherein the microcontroller utilizes timing to select a program from the one or more stored programs to produce either daytime or nighttime ultradian brainwave activity pattern signals.

11. The apparatus of claim 8, wherein a premises power-line is capacitively coupled to the mixed bi-polar square wave signal using non-polarized capacitors rated at least two times the RMS voltage of the premises power-line and between 1,000 and 470,000 picofarads.

12. The apparatus of claim 8, where the second frequency is in the range of 500,000 Hz to 2,400,000 Hz.

13. The apparatus of claim 8, where the first frequency is in the range of 1 Hz to 500,000 Hz.

14. An apparatus for entraining brainwaves in mammals, comprising:

a microcontroller;

a means for clocking the microcontroller at a frequency within 1% of a Fibonacci number in the range of 75,000 Hz to 102,000,000 Hz;

a storage device storing one or more programs, said programs being timed frequency sequences corresponding at least in part to an ultradian brainwave activity pattern of mammals; and the storage device further storing instructions for controlling the microcontroller to perform steps comprising:

producing a first square wave signal having a first frequency in the range of 1 Hz to 5,000 Hz based at least in part upon the microcontroller's clocking frequency and a brainwave activity pattern of a mammal in said one or more stored programs;

producing a second square wave signal having a second frequency in the range of 500,000 Hz to 2,400,000 Hz based at least in part upon the microcontroller's clocking frequency and the one or more stored programs;

producing a mixed bi-polar square wave signal by mixing the first square wave signal and the second square wave signal through an H-bridge acting as an eXclusive OR (XOR) to modulate the first and second square wave signals;

injecting the mixed bi-polar square wave signal on to premises power-line using non-polarized capacitors rated at least two times the RMS voltage of the premises power-line and between 1,000 and 470,000 picofarads.

* * * * *